United States Patent [19]  [11] 4,448,717
Shuman  [45] May 15, 1984

[54] PHARMACOLOGICALLY ACTIVE PEPTIDES

[75] Inventor: Robert T. Shuman, Greenwood, Ind.

[73] Assignee: Eli Lilly and Company, Indianapolis, Ind.

[21] Appl. No.: 441,137

[22] Filed: Nov. 12, 1982

[51] Int. Cl.³ .......................................... C07C 103/52
[52] U.S. Cl. .............................................. 260/112.5 E
[58] Field of Search .................. 260/112.5 R, 112.5 E

[56] References Cited

U.S. PATENT DOCUMENTS

| | | | |
|---|---|---|---|
| 4,264,491 | 4/1981 | Smithwick et al. | 260/112.5 R |
| 4,265,808 | 5/1981 | Gesellchen et al. | 260/112.5 R |
| 4,322,340 | 3/1982 | Shuman et al. | 260/112.5 E |
| 4,333,873 | 6/1982 | Shuman | 260/112.5 E |

OTHER PUBLICATIONS

Hughes et al., *Nature,* 258, 577, (1975).
Buscher et al., *Nature,* 261, 423, (1976).
Kiso et al., Naturwissenschaften 68, 210–212, (1981).

*Primary Examiner*—Delbert R. Phillips
*Assistant Examiner*—F. T. Moezie
*Attorney, Agent, or Firm*—William C. Martens; Arthur R. Whale

[57] ABSTRACT

Compounds of the formula $$R-Tyr-A-Gly-N(R_1)-CH(CH_2C_6H_4X)-C(=O)-Z$$

and pharmaceutically acceptable non-toxic acid addition salts thereof, in which

R is hydrogen, methyl, ethyl, cyclopropylmethyl, or allyl;

A is a residue of a D-amino acid selected from the group consisting of Ala, Abu, Nva, Val, Nle, Leu, Ile, Gly(Al), Gly(Cp), Met, Cys(Me), Met(O), Cys(Me) (O), Ser, Ser(Me), Thr, and Hse;

$R_1$ is hydrogen, $C_1$–$C_3$ primary alkyl, cyclopropylmethyl, allyl, ethylthiomethyl, 2-fluoroethyl, or propargyl;

X is fluoro, bromo, iodo, chloro, hydroxy, $C_1$–$C_3$ alkyl, trifluoromethyl, or $C_1$–$C_2$ alkoxy; and Z is methyl or ethyl; are useful analgesic agents.

15 Claims, No Drawings

PHARMACOLOGICALLY ACTIVE PEPTIDES

Background of the Invention

This invention relates to a novel class of compounds which exhibit analgesic activity.

Recently, endogenous substances having morphine-like properties have been extracted from mammalian brain or csf. These substances, named enkephalin, have been identified by Hughes et al., Nature, 258, 577 (1975) as pentapeptides having the following sequences:

H-Tyr-Gly-Gly-Phe-Met-OH
H-Tyr-Gly-Gly-Phe-Leu-OH.

These compounds are referred to as methionine-enkephalin and leucine-enkephalin, respectively.

Although methionine and leucine enkephalin have been shown to exhibit analgesic activity in mice upon administration intracerebroventricularly [Buscher et al., Nature, 261, 423 (1976)], they are practically devoid of any useful analgesic activity when administered parenterally.

Therefore, since the discovery of the enkephalins, much effort has been devoted to preparing analogs of the enkephalins in the hope of finding compounds having enhanced activity and practical utility due to their bioavailability by parenteral or oral administration.

Dutta et al., Life Sciences 21, pp. 559-562 (1977) report certain structure modifications which, they suggest, tend to enhance potency. They suggest activity can be enhanced by any or all of the following:

(a) substitution of Gly in position 2 by certain D- or α-aza-amino acids;

(b) conversion of the terminal carboxyl to the methyl ester or the amide;

(c) modification of the Phe in the 4-position by α-aza substitution, N-methylation, or hydrogenation of the aromatic ring.

In addition, Roemer et al., Nature 268, pp. 547-549 (1977), suggest modification of the Met[5] to its corresponding carbinol and oxidation of the Met sulfur to the sulfoxide as useful modifications.

Another structural modification of significance is that reported in U.S. Pat. No. 4,322,342. This publication suggests enhancement of activity and bioavailability of enkephalin analogs by insertion of a D-amino acid residue in position 2, conversion of the terminal carboxyl to an amide, and N-alkylation of the amino acid residue in position 5.

Kiso et al., Naturwissenschaften 68, 210-212 (1981), describe tetrapeptides having a carbinol terminal, specifically Tyr-D-Ala-Gly-Phe-OL, Tyr-D-Met(O)-Gly-Phe-OL, and related such structures.

A new class of compounds has been discovered which exhibit analgesic activity. These compounds are analogs of enkephalin tetrapeptides in which the normally C-terminal amino acid has been replaced by a methyl or ethyl ketone.

SUMMARY OF THE INVENTION

Thus, this invention relates to a class of compounds having the formula

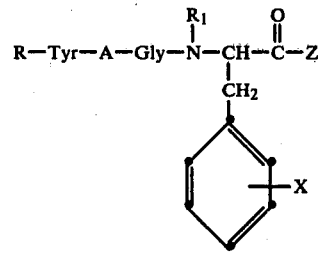

and pharmaceutically acceptable non-toxic acid addition salts thereof, in which

R is hydrogen, methyl, ethyl, cyclopropylmethyl, or allyl;

A is a residue of a D-amino acid selected from the group consisting of Ala, Abu, Nva, Val, Nle, Leu, Ile, Gly(Al), Gly(Cp), Met, Cys(Me), Met(O), Cys(Me)(O), Ser, Ser(Me), Thr, and Hse;

$R_1$ is hydrogen, $C_1$-$C_3$ primary alkyl, cyclopropylmethyl, allyl, ethylthiomethyl, 2-fluoroethyl, or propargyl;

X is fluoro, bromo, iodo, chloro, hydroxy, $C_1$-$C_3$ alkyl, trifluoromethyl, or $C_1$-$C_2$ alkoxy; and Z is methyl or ethyl.

DETAILED DESCRIPTION OF THE INVENTION

As indicated above, the compounds of this invention have the following structure:

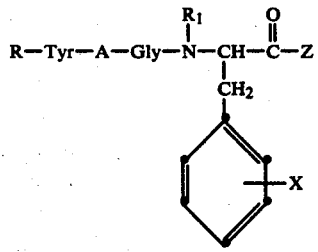

Also included are the pharmaceutically acceptable non-toxic acid addition salts of these compounds.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts are prepared by conventional methods.

As will be noted from the definition of the various substituents which appear in the above structure, the compounds which are defined by this structure are tetrapeptides, the C-terminal portion of which is a methyl or ethyl ketone.

The stereoconfiguration of the compounds of this invention is an essential feature thereof. For the sake of convenience, the amino acid residues of the tetrapeptides of this invention are numbered sequentially beginning with the residue at the terminal amino function. The chirality of the amino acid residues, reading from Position 1 through Position 4, is L, D, none, and L. The residue in Position 3 is a glycine moiety, and, thus, no chirality as to this residue exists.

The group $R_1$ as used herein is defined to include the group "$C_1-C_3$ primary alkyl". By the term "$C_1-C_3$ primary alkyl" is meant methyl, ethyl, and n-propyl.

The group X as used herein is defined to include the group "$C_1-C_3$ alkyl". By the term "$C_1-C_3$ alkyl" is intended methyl, ethyl, n-propyl and isopropyl.

The group X as used herein is defined to include the group "$C_1-C_2$ alkoxy". By the term "$C_1-C_2$ alkoxy" is meant methoxy and ethoxy.

With respect to the particular position residues of the tetrapeptides of this invention, the following considerations prevail:

(A). Position 1

This position represents the amino-terminal portion of the peptide. The residue is that which results from L-tyrosine. The residue can be N-unsubstituted, in which case R is hydrogen. Moreover, the residue can be N-mono-substituted, giving rise to N-methyl, N-ethyl-, N-cyclopropylmethyl-, or N-allyl-. For compounds having exceptionally high levels of analgesic activity when administered parenterally, the tyrosyl residue which is present in Position 1 preferably is N-unsubstituted. For compounds having exceptionally high levels of analgesic activity when administered orally, the tyrosyl residue preferably is N-substituted. In the event that the tyrosyl is N-substituted, the N-substituent preferably is methyl.

(B). Position 2.

The amino acid residue (A) which is present in the second position of the peptides of this invention must be the D stereoisomer and is any of several α-amino acid residues depending upon the substituent ($R_4$) on the α-carbon. These include residues derived from D-alanine (Ala) ($R_4$ is methyl), D-α-aminobutyric acid (Abu) ($R_4$ is ethyl), D-norvaline (Nva) ($R_4$ is n-propyl), D-valine (Val) ($R_4$ is isopropyl), D-norleucine (Nle) ($R_4$ is n-butyl), D-leucine (Leu) ($R_4$ is isobutyl), D-isoleucine (Ile) ($R_4$ is sec-butyl), D-allylglycine [Gly(Al)] ($R_4$ is allyl), D-cyclopropylmethylglycine [Gly(Cp)] ($R_4$ is cyclopropylmethyl), D-methionine (Met) ($R_4$ is 2-methylthioethyl), D-(S-methyl)cysteine [Cys(Me)] ($R_4$ is methylthiomethyl), D-methionine sulfoxide [Met(O)] ($R_4$ is methylsulfinylethyl), D-(S-methyl)cysteine sulfoxide [Cys(Me)(O)] ($R_4$ is methylsulfinylmethyl), D-serine (Ser) ($R_4$ is hydroxymethyl), D-threonine (Thr) ($R_4$ is 1-hydroxyethyl), and D-homoserine (Hse) ($R_4$ is 2-hydroxyethyl). Preferably, A is Ala, Nva, Val, Nle, Leu, Ile, Ser, Met, Met(O), Thr, Hse, or Ser(Me), and, more preferably, is Ala, Met, Met(O), Nva, Ser(Me), or Nle. Most preferably, A is Ala.

(C). Position 3.

The amino acid residue present in this position is that derived from glycine (Gly).

(D). Position 4

The moiety present in this position is not, strictly speaking, an amino acid residue. Instead, it is a ketone corresponding to L-phenylalanine or to a ring-substituted L-phenylalanine. The moiety so defined and joined to the remainder of the molecule through —NR$_1$— is 2-oxo-1-benzylpropyl, 2-oxo-1-benzylbutyl, or a ring-substituted derivative of each. If the ring is substituted, it preferably is mono-substituted in the meta or para position and, if substituted, preferably is fluoro, bromo, iodo, chloro, methyl, ethyl, n-propyl, isopropyl, trifluoromethyl, methoxy, or ethoxy. If substituted, the substituent preferably is p-fluoro, m-bromo or m-methyl.

The joining amino moiety (—NR$_1$—) may be unsubstituted (R$_1$ is hydrogen) or substituted. If substituted, R$_1$ is methyl, ethyl, n-propyl, cyclopropylmethyl, allyl, ethylthiomethyl, 2-fluoroethyl, or propargyl. Preferably, R$_1$ is C$_1$-C$_3$ primary alkyl, allyl, cyclopropylmethyl, or propargyl. Most preferably, R$_1$ is ethyl, cyclopropylmethyl, allyl, or propargyl.

In this specification, the following abbreviations, most of which are well known and are commonly used in the art, are employed:

Abu—α-aminobutyric acid
Ala—alanine
Cys—cysteine
Cys(Me)—(S-methyl)cysteine
Cys(Me)(O)—(S-methyl)cysteine sulfoxide
Gly—glycine
Gly(Al)—allylglycine
Gly(Cp)—cyclopropylmethylglycine
Hse—homoserine
Ile—isoleucine
Leu—leucine
Met—methionine
Met(O)—methionine sulfoxide
Nle—norleucine
Nva—norvaline
Phe—phenylalanine
Ser—serine
Ser(Me)—O-methylserine
Thr—threonine
Tyr—tyrosine
Val—valine
Ac—acetyl
AcOMe—acetoxymethyl
Al—allyl
Cp—cyclopropylmethyl
Me—methyl
Et—ethyl
Ip—isopropyl
Pr—n-propyl
OMe—methoxy
Etm—ethylthiomethyl
Fle—2-fluoroethyl
Ppg—propargyl
Bu—n-butyl
i-Bu—isobutyl
t-Bu—t-butyl
s-Bu—sec-butyl
Boc—t-butyloxycarbonyl
Bzl—benzyl
Cbz—benzyloxycarbonyl
DCC—N,N'-dicyclohexylcarbodiimide
HBT—1-hydroxybenzotriazole
DMF—N,N-dimethylformamide
TFA—trifluoroacetic acid
THF—tetrahydrofuran
DEAE—diethylaminoethyl
NMM—N-methylmorpholine
IBCF—isobutyl chloroformate
18-crown-6—1,4,7,10,13,16-hexaoxacyclooctadecane Examples of typical compounds of this invention are the following, any or all of which may be in the form of a pharmaceutically acceptable nontoxic acid addition salt. In each of the following, the designation (Phe-Me) represents phenylalanine derivatized to its methyl ketone, and the designation (Phe-Et) represents phenylalanine derivatized to its ethyl ketone. The presence of any ring substitution is noted in parenthesis following the Phe designation.

H-L-Tyr-D-Ala-Gly-L-(N-Me)Phe-Me;
H-L-Tyr-D-Ala-Gly-L-(N-Et)Phe-Me;
H-L-Tyr-D-Abu-Gly-L-(N-Pr)Phe(m-Br)-Me;
H-L-Tyr-D-Abu-Gly-L-(N-Et)Phe-Me;
H-L-Tyr-D-Nva-Gly-L-(N-Ppg)Phe(p-Me)-Me;
H-L-Tyr-D-Nva-Gly-L-(N-Et)Phe(m-OMe)-Me;
H-L-Tyr-D-Val-Gly-L-(N-Et)Phe(p-F)-Me;
H-L-Tyr-D-Val-Gly-L-(N-Pr)Phe(p-Cl)-Me;
H-L-Tyr-D-Nle-Gly-L-Phe(m-I)-Me;
H-L-Tyr-D-Nle-Gly-L-(N-Ppg)Phe-Me;
H-L-Tyr-D-Leu-Gly-L-(N-Etm)Phe-Me;
H-L-Tyr-D-Leu-Gly-L-Phe-Me;
H-L-Tyr-D-Ile-Gly-L-(N-Al)Phe(m-Br)-Me;
H-L-Tyr-D-Ile-Gly-L-(N-Cp)Phe(p-Et)-Me;
H-L-Tyr-D-Ala-Gly-L-(N-Et)Phe(p-OH)-Me;
H-L-Tyr-D-Ala-Gly-L-Phe(p-Oet)-Me:
H-L-Tyr-D-Ala-Gly-L-(N-Fle)Phe(o-Cl)-Me;
H-L-Tyr-D-Ala-Gly-L-(N-Etm)Phe(m-I)-Me;
H-L-Tyr-D-Ala-Gly-L-(N-Fle)Phe(p-I)-Me;
H-L-Tyr-D-Ala-Gly-L-Phe-Me;
H-L-Tyr-D-Ala-Gly-L-Phe-Me;
H-L-Tyr-D-Ala-Gly-L-(N-Al)Phe-Me;
H-L-Tyr-D-Ala-Gly-L-(N-Ppg)Phe-Me;
H-L-Tyr-D-Thr-Gly-L-(N-Cp)Phe-Me;
H-L-Tyr-D-Val-Gly-L-(N-Et)Phe-Me;
H-L-Tyr-D-Leu-Gly-L-(N-Et)Phe(m-Br)-Me;
H-L-Tyr-D-Val-Gly-L-Phe(m-Br)-Me;
H-L-Tyr-D-Leu-Gly-L-(N-Al)Phe(p-F)-Me;
H-L-Tyr-D-Thr-Gly-L-Phe(p-CF3)-Me;
H-L-Tyr-D-Thr-Gly-L-(N-Et)Phe(p-OEt)-Me;
H-L-Tyr-D-Thr-Gly-L-(N-Me)Phe(m-Br)-Me;
H-L-Tyr-D-Thr-Gly-L-(N-Pr)Phe(p-Br)-Me;
H-L-Tyr-D-Thr-Gly-L-(N-Al)Phe(m-Cl)-Me;
H-L-Tyr-D-Gly(Al)-Gly-L-(N-Et)Phe(p-Et)-Me;
H-L-Tyr-D-Gly(Cp)-Gly-L-(N-Me)Phe-Me;
H-L-Tyr-D-Met-Gly-L-(N-Et)Phe-Me;
H-L-Tyr-D-Cys(Me)-Gly-L-(N-Cp)Phe(o-Br)-Me;
H-L-Tyr-D-Met(O)-Gly-L-(N-Pr)Phe-Me;
H-L-Tyr-D-Cys(Me)(O)-Gly-L-Phe(m-Br)-Me;
H-L-Tyr-D-Ser-Gly-L-Phe(m-I)-Me;
H-L-Tyr-D-Ser-Gly-L-(N-Et)Phe(p-Cl)-Me;
(N-Me)-L-Tyr-D-Ala-Gly-L-(N-Cp)Phe-Me;
(N-Me)-L-Tyr-D-Thr-Gly-L-(N-Et)Phe(p-I)-Me;
H-L-Tyr-D-Hse-Gly-L-(N-Cp)Phe-Me;
(N-Me)-L-Tyr-D-Ala-Gly-L-Phe-Me;
(N-Me)-L-Tyr-D-Ala-Gly-L-(N-Me)Phe(m-Br)-Me;
(N-Me)-L-Tyr-D-Ala-Gly-L-(N-Pr)Phe-Me;
(N-Et)-L-Tyr-D-Abu-Gly-L-(N-Cp)Phe(p-I)-Me;
(N-Me)-L-Tyr-D-Val-Gly-L-Phe(p-Pr)-Me;
(N-Pr)-L-Tyr-D-Leu-Gly-L-(N-Cp)Phe(p-CF3)-Me;
H-L-Tyr-D-Abu-Gly-L-(N-Al)Phe(m-OMe)-Me;
H-L-Tyr-D-Nle-Gly-L-(N-Al)Phe(o-Br)-Me;
H-L-Tyr-D-Ile-Gly-L-(N-Ppg)Phe(p-Br)-Me;
(N-Me)-L-Tyr-D-Leu-Gly-L-(N-Et)Phe(m-Br)-Me;
(N-Me)-L-Tyr-D-Nva-Gly-L-(N-Me)Phe(p-Ip)-Me;
(N-Me)-L-Tyr-D-Ala-Gly-L-(N-Ppg)Phe(p-Pr)-Me;
(N-Et)-L-Tyr-D-Ala-Gly-L-(N-Me)Phe-Me;
(N-Cpm)-L-Tyr-D-Ala-Gly-L-(N-Me)Phe-Me;
(N-Me)-L-Tyr-D-Ala-Gly-L-(N-Cp)Phe-Me;
(N-Al)-L-Tyr-D-Ala-Gly-L-(N-Al)Phe-Me;
(N-Me)-L-Tyr-D-Ala-Gly-L-(N-Etm)Phe-Me;
(N-Et)-L-Tyr-D-Ala-Gly-L-(N-Et)Phe-Me;
(N-Cpm)-L-Tyr-D-Ala-Gly-L-(N-Et)Phe(m-Me)-Me;
(N-Me)-L-Tyr-D-Ala-Gly-L-(N-Al)Phe(p-OEt)-Me;
H-L-Tyr-D-Ala-Gly-L-(N-Me)Phe-Et;
H-L-Tyr-D-Ala-Gly-L-(N-Et)Phe-Et;
H-L-Tyr-D-Abu-Gly-L-(N-Cp)Phe(m-Br)-Et;
H-L-Tyr-D-Abu-Gly-L-(N-Et)Phe(p-Br)-Et;
H-L-Tyr-D-Nva-Gly-L-(N-Cp)Phe(m-OMe)-Et;
H-L-Tyr-D-Nva-Gly-L-(N-Et)Phe(p-CF3)-Et;
H-L-Tyr-D-Val-Gly-L-(N-Cp)Phe-Et;
H-L-Tyr-D-Val-Gly-L-(N-Pr)Phe(p-F)-Et;
H-L-Tyr-D-Nle-Gly-L-(N-Cp)Phe(o-OMe)-Et;
H-L-Tyr-D-Nle-Gly-L-(N-Ppg)Phe(m-Br)-Et;
H-L-Tyr-D-Leu-Gly-L-(N-Etm)Phe(p-I)-Et;
H-L-Tyr-D-Leu-Gly-L-(N-Cp)Phe(m-Me)-Et;
H-L-Tyr-D-Ile-Gly-L-(N-Al)Phe(o-OMe)-Et;
H-L-Tyr-D-Ile-Gly-L-(N-Cp)Phe-Et;
H-L-Tyr-D-Ala-Gly-L-Phe-Et;
H-L-Tyr-D-Ala-Gly-L-(N-Pr)Phe(m-Br)-Et;
H-L-Tyr-D-Ala-Gly-L-(N-Fle)Phe(p-I)-Et;
H-L-Tyr-D-Ala-Gly-L-(N-Etm)Phe(o-Cl)-Et;
H-L-Tyr-D-Ala-Gly-L-(N-Fle)Phe-Et;
H-L-Tyr-D-Ala-Gly-L-(N-Fle)Phe(m-Br)-Et;
H-L-Tyr-D-Ala-Gly-L-(N-Cp)Phe(m-Me)-Et;
H-L-Tyr-D-Ala-Gly-L-(N-Al)Phe(o-CF3)-Et;
H-L-Tyr-D-Ala-Gly-L-(N-Ppg)Phe(m-OEt)-Et;
H-L-Tyr-D-Thr-Gly-L-(N-Et)Phe(m-Br)-Et;
H-L-Tyr-D-Val-Gly-L-(N-Et)Phe-Et;
H-L-Tyr-D-Leu-Gly-L-Phe-Et;
H-L-Tyr-D-Val-Gly-L-(N-Al)Phe(p-I)-Et;
H-L-Tyr-D-Leu-Gly-L-(N-Al)Phe-Et;
H-L-Tyr-D-Thr-Gly-L-(N-Cp)Phe(p-F)-Et;
H-L-Tyr-D-Thr-Gly-L-(N-Et)Phe-Et;
H-L-Tyr-D-Thr-Gly-L-Phe(m-OMe)-Et;
H-L-Tyr-D-Thr-Gly-L-(N-Pr)Phe(m-Pr)-Et;
H-L-Tyr-D-Thr-Gly-L-(N-Al)Phe(p-Br)-Et;
H-L-Tyr-D-Gly(Al)-Gly-L-(N-Cp)Phe(m-Cl)-Et;
H-L-Tyr-D-Gly(Cp)-Gly-L-Phe-Et;
H-L-Tyr-D-Met-Gly-L-(N-Et)Phe-Et;
H-L-Tyr-D-Cys(Me)-Gly-L-(N-Cp)Phe-Et;
H-L-Tyr-D-Met(O)-Gly-L-(N-Pr)Phe-Et;
H-L-Tyr-D-Cys(Me)(O)-Gly-L-(N-Cp)Phe(p-Pr)-Et;
H-L-Tyr-D-Ser-Gly-L-(N-Cp)Phe(o-Br)-Et;
H-L-Tyr-D-Ser-Gly-L-Phe-Et;
(N-Me)-L-Tyr-D-Ala-Gly-L-(N-Cp)Phe-Et;
(N-Me)-L-Tyr-D-Thr-Gly-L-(N-Et)Phe(m-Br)-Et;
H-L-Tyr-D-Hse-Gly-L-(N-Et)Phe-Et;
(N-Me)-L-Tyr-D-Ala-Gly-L-(N-Et)Phe(m-Ip)-Et;
(N-Me)-L-Tyr-D-Ala-Gly-L-(N-Me)Phe(p-Et)-Et;
(N-Me)-L-Tyr-D-Ala-Gly-L-(N-Pr)Phe(p-CF3)-Et;
(N-Et)-L-Tyr-D-Abu-Gly-L-(N-Cp)Phe(o-Cl)-Et;
(N-Me)-L-Tyr-D-Val-Gly-L-Phe-Et;
(N-Pr)-L-Tyr-D-Leu-Gly-L-(N-Cp)Phe-Et;
H-L-Tyr-D-Abu-Gly-L-(N-Al)Phe(m-I)-Et;
H-L-Tyr-D-Nle-Gly-L-(N-Al)Phe(p-OMe)-Et;
H-L-Tyr-D-Ile-Gly-L-(N-Ppg)Phe(p-CF3)-Et;
(N-Me)-L-Tyr-D-Leu-Gly-L-(N-Et)Phe(m-Br)-Et;
(N-Me)-L-Tyr-D-Nva-Gly-L-(N-Me)Phe(m-Br)-Et;
(N-Me)-L-Tyr-D-Ala-Gly-L-(N-Ppg)Phe(m-I)-Et;
(N-Et)-L-Tyr-D-Ala-Gly-L-(N-Me)Phe-Et;
(N-Cpm)-L-Tyr-D-Ala-Gly-L-Phe(p-CF3)-Et;
(N-Me)-L-Tyr-D-Ala-Gly-L-(N-Cp)Phe(m-OMe)-Et;
(N-Al)-L-Tyr-D-Ala-Gly-L-(N-Al)Phe(p-Pr)-Et;
(N-Me)-L-Tyr-D-Ala-Gly-L-(N-Fle)Phe(m-Br)-Et;
(N-Et)-L-Tyr-D-Ala-Gly-L-Phe(m-Br)-Et;
(N-Al)-L-Tyr-D-Ala-Gly-L-(N-Et)Phe-Et;
(N-Me)-L-Tyr-D-Ala-Gly-L-(N-Al)Phe-Et;
and the like.

The compounds of this invention are prepared by routine methods for peptide synthesis. It is possible, during the synthesis of certain of the compounds of this invention, that partial racemization can occur. However, the extent of racemization, should such occur, is not sufficient to significantly alter the analgesic activity of the compounds of this invention.

The compounds of this invention can be synthesized by classical solution phase synthesis.

Preparation involves the coupling of amino acids or peptide fragments by reaction of the carboxyl function of one with the amino function of another to produce an amide linkage. In order to effectively achieve coupling, it is desirable, first, that all reactive functionalities not participating directly in the reaction be inactivated by the use of appropriate blocking groups, and, secondly, that the carboxyl function which is to be coupled be appropriately activated to permit coupling to proceed. All of this involves a careful selection of both reaction sequence and reaction conditions as well as utilization of specific blocking groups so that the desired peptide product will be realized. Each of the amino acids which is employed to produce the compounds of this invention and which has the particularly selected protecting groups and/or activating functionalities is prepared by techniques well recognized in the peptide art.

Selected combinations of blocking groups are employed at each point of the total synthesis of the compounds of this invention. These particular combinations have been found to function most smoothly. Other combinations would operate in the synthesis of the compounds of this invention, although, perhaps, with a lesser degree of success. Thus, for example, benzyloxycarbonyl, t-butyloxycarbonyl, t-amyloxycarbonyl, p-methoxybenzyloxycarbonyl, adamantyloxycarbonyl, and isobornyloxycarbonyl can be variously employed as amino blocking groups in the synthesis of the compounds of this invention. Furthermore, benzyl (Bzl) generally is employed as the hydroxy-protecting group for the tyrosyl residue even though others, such as p-nitrobenzyl (PNB), p-methoxybenzyl (PMB), and the like, could well be employed.

The carboxyl blocking groups used in preparing the compounds of this invention can be any of the typical ester-forming groups, including, for example, methyl, ethyl, benzyl, p-nitrobenzyl, p-methoxybenzyl, 2,2,2-trichloroethyl, and the like.

Coupling of the suitably protected N-blocked amino acid or peptide fragment with a suitably protected carboxy-blocked amino acid or peptide fragment in preparation of the compounds of this invention consists of rendering the free carboxyl function of the amino acid or peptide fragment active to the coupling reaction. This can be accomplished using any of several well recognized techniques. One such activation technique involves conversion of the carboxyl function to a mixed anhydride. The free carboxyl function is activated by reaction with another acid, typically a derivative of carbonic acid, such as an acid chloride thereof. Examples of acid chlorides used to form mixed anhydrides are ethyl chloroformate, phenyl chloroformate, sec-butyl chloroformate, isobutyl chloroformate, pivaloyl chloride, and the like. Preferably, isobutyl chloroformate is employed.

Another method of activating the carboxyl function for the purpose of carrying out the coupling reaction is by conversion to its active ester derivative. Such active esters include, for example, a 2,4,5-trichlorophenyl ester, a pentachlorophenyl ester, a p-nitrophenyl ester, and the like. Another coupling method available for use is the well-recognized azide coupling method.

The preferred coupling method in preparation of the compounds of this invention involves the use of N,N'-dicyclohexylcarbodiimide (DCC) to activate the free carboxyl function thereby permitting coupling to proceed. This activation and coupling technique is carried out employing an equimolar quantity of DCC relative to the amino acid or peptide fragment and is carried out in the presence of an equimolar quantity of 1-hydroxybenzotriazole (HBT). The presence of HBT suppresses undesirable side reactions including the possibility of racemization.

Cleavage of selected blocking groups is necessary at particular points in the synthetic sequence employed in preparation of the compounds of this invention. A chemist of ordinary skill in the art of peptide synthesis can readily select from representative protecting groups those groups which are compatible in the sense that selective cleavage of the product can be accomplished permitting removal of one or more but less than all of the protecting groups present on the amino acid or peptide fragment. These techniques are well recognized in the peptide art. A more complete discussion of the techniques which are available for selective cleavage is provided in the literature in Schröder and Lübke, *The Peptides*, Volume I, Academic Press, New York, (1965), and especially in the Table provided at pages 72–75 thereof.

Cleavage of carboxyl protecting groups can be accomplished by alkaline saponification. Relatively strong alkaline conditions, typically using an alkali metal hydroxide, such as sodium hydroxide, potassium hydroxide, lithium hydroxide, and the like, are generally employed to deesterify the protected carboxyl. The reaction conditions under which saponification is accomplished are well recognized in the art. Many of the carboxyl blocking groups also can be removed by catalytic hydrogenolysis including, for example, hydrogenolysis in the presence of a catalyst such as palladium on carbon. Furthermore, in those instances in which the carboxyl blocking group is p-nitrobenzyl or 2,2,2-trichloroethyl, deblocking can be accomplished by reduction in the presence of zinc and hydrochloric acid.

Many of the amino blocking groups are cleaved by treating the protected amino acid or peptide with an acid such as formic acid, trifluoroacetic acid (TFA), p-toluenesulfonic acid (TSA), benzenesulfonic acid (BSA), naphthalenesulfonic acid, and the like, to form the respective acid addition salt product. Cleavage of others can be accomplished by treating the blocked amino acid or peptide with a mixture of HBr and acetic acid to produce the corresponding hydrobromide acid addition salt. The particular method or reagent which is employed will depend upon the chemical or physical characteristics of the materials involved in the specific deblocking reaction. The resulting acid addition salt can be converted to a more pharmaceutically acceptable form by treatment with a suitable ion exchange resin, such as DEAE Sephadex A25, Amberlyst A27, and the like.

The hydroxy-protecting group can be retained on the peptide throughout the sequence of its preparation, being removed during the final synthetic step in conjunction with cleavage of the amino blocking group. However, depending upon the conditions employed for removal of the carboxyl blocking group, it may be removed earlier in the preparative sequence. When the carboxyl group is cleaved by alkaline saponification, the hydroxy-protecting group is retained; however, when catalytic hydrogenolysis is employed for removal of the carboxyl protecting group, the hydroxy protecting group also is cleaved. The latter situation does not represent a serious problem since preparation of the compounds of this invention can be accomplished in the presence of an unprotected tyrosyl residue.

A preferred specific method for preparing the compounds of this invention involves coupling a dipeptide representing the amino acid residues in the 2- and 3-positions with the C-terminal amino acid following which the resulting tripeptide is coupled to the N-terminal tyrosine. The C-terminal amino acid can be structured so as to contain the methyl or ethyl ketone moiety. The general sequence is depicted by the scheme provided hereinbelow. In the sequence, the letter Z represents the C-terminal moiety, the symbol AA represents an amino acid residue, and the number appended to the symbol AA represents the position of the amino acid in the ultimate peptide product sequence.

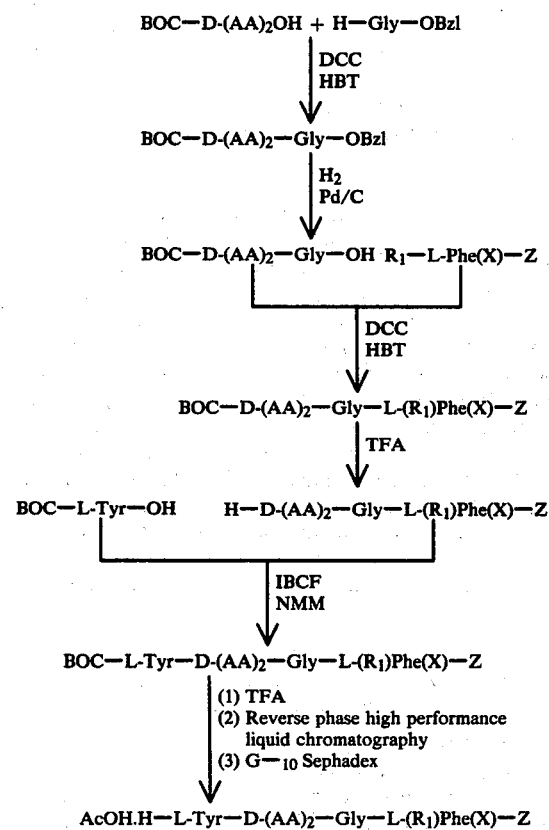

The above represents only one sequence for preparing compounds of this invention. Other sequences, of course, are available. One involves coupling a separately prepared N-terminal tripeptide with a separately prepared C-terminal methyl or ethyl ketone followed by appropriate deblocking of any remaining blocked moieties. Another solution method which can be employed involves the step-wise, sequential addition of single amino acids in construction of the peptide chain beginning with the C-terminal methyl or ethyl ketone moiety. Reaction techniques such as those described above are employed in this as well as any other contemplated preparative sequence.

In certain of the compounds of this invention, one or more of the groups R and $R_1$ are, variously, alkyl, allyl, propargyl, ethylthiomethyl, 2-fluoroethyl, or cyclopropylmethyl. In these instances, the appropriate N-substituted amino acid is employed in the preparative sequence. Any of the N-monosubstituted amino acids can be prepared as follows using an N-protected amino acid as starting material:

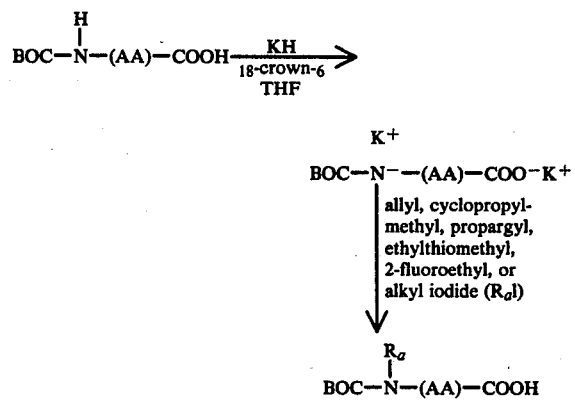

As the above sequence indicates, the amino acid first is treated with potassium hydride in the presence of a suitable crown ether to generate the dianion. The intermediate then is treated with the appropriate allyl, cyclopropylmethyl, propargyl, ethylthiomethyl, 2-fluoroethyl, or alkyl iodide to obtain the desired N-substituted amino acid.

It will be apparent to those of ordinary skill in the art of peptide synthesis that racemization at the α-carbon can occur under strongly alkaline conditions such as those employed in the above alkylation procedure. The degree of racemization may vary depending upon the particular amino acid which is involved. Racemization can be minimized by using excess alkylating agent and by keeping the reaction time as short as possible. Nevertheless, even if racemization occurs, the product can be purified by recrystallization as the salt of d(+) α-phenylethylamine.

The compounds of this invention are valuable pharmaceutical agents. They exhibit analgesic activity and also neuroleptic activity. They are especially useful in alleviation of pain and amelioration of emotional disturbances when administered parenterally or orally to mammals, including humans.

The compounds of this invention may be administered alone or in combination with pharmaceutically acceptable carriers, the proportion of which is determined by the solubility and chemical nature of the compound, the selected route of administration, and standard pharmaceutical practice.

Preferred compositions are those suitable for parenteral administration, that is, intramuscular, subcutaneous, or intravenous. These include sterile, injectable solutions or suspensions, and sterile injectable depot or slow-release formulations. Particularly convenient sterile, injectable solutions are made up in isotonic saline or isotonic dextrose. The sterile, injectable compositions can be prepared and stored as such or they can be prepared immediately prior to use by adding a sterile medium, for example, water, to a known weight of sterile ingredient enclosed in a vehicle, for example, a vial or an ampoule, which maintains sterility of the ingredient. The known weight of sterile ingredient may also contain sufficient sterile dextrose or sodium chloride to provide an isotonic solution or suspension after addition of the sterile medium.

Preferred compositions also are those suitable for oral administration. These can be prepared as discrete units such as capsules, tablets, and the like, each containing a predetermined amount of the active ingredient. Moreover, they, for example, can be prepared in powder or granule form, as a solution or a suspension in an aqueous or a non-aqueous medium, or as an emulsion.

The tablet can be prepared by compression, generally with one or more accessory ingredients. The tablets are prepared by compressing the active ingredient in a free-flowing form, such as a powder or granule, and generally mixed with one or more other ingredients, such as binders, lubricants, inert diluents, lubricating agents, surface active agents, buffers, flavoring agents, thickeners, preservatives, dispensing agents, and the like.

Physicians will determine the particular dosage of the compounds of this invention which is most suitable. The selected dosages will vary depending upon the mode of administration, the particular compound administered, the patient under treatment, and the kind of treatment. In general, however, the dosage will range from about 0.5 μg. to about 2 mg. per kilogram body weight of the recipient, and, preferably, from about 10 μg. to about 100 μg, per kilogram body weight, when administered intramuscularly or subcutaneously, and from about 0.1 μg. to about 200 μg. per kilogram body weight of the recipient, and, preferably, from about 1 μg, to about 50 μg, per kilogram body weight, when administered intravenously. When administered orally, the dosage generally will range from about 100 μg. to about 100 mg. per kilogram body weight of the recipient, and, preferably, from about 500 μg. to about 50 mg. per kilogram body weight, and, more preferably, from about 1 mg. to about 10 mg. per kilogram body weight.

The following examples are provided to illustrate the preparation and activity of the compounds of this invention. They are not intended to be limiting upon the scope thereof.

EXAMPLE 1

Preparation of L-Tyrosyl-D-alanyl-N-(2-oxo-1-benzylpropyl)glycinamide, Acetate Salt A. 3-(t-Butyloxycarbamido)-4-phenylbutan-2-one To a stirred solution of 15.9 g. (0.06 mole) of $N^\alpha$-t-butyloxycarbonyl-L-phenylalanine in 100 ml. of anhydrous ethyl ether at room temperature and maintained under a nitrogen atmosphere were added 13.0 ml. (0.13 mole) of 1N methyllithium dropwise over a 30 minute period. The resulting mixture was stirred for an additional 6 hours at room temperature after which water (25 ml.) was added dropwise. The reaction mixture was diluted with water and ethyl acetate, and the resulting mixture was placed in a separatory funnel. The ethyl acetate layer was separated and washed with 1.5N citric acid followed by water. The ethyl acetate layer was then dried over magnesium sulfate and concentrated in vacuo to an oil. The oil was placed on the 10×2 cm. column containing Grace and Davison grade 62 silica gel in methylene chloride. The column was eluted with a $CH_2Cl_2$—$CHCl_3$ step gradient [$CH_2Cl_2 \rightarrow CH_2Cl_2$—$CHCl_3$ (50/50)]. The resulting eluted fractions were combined according to the thin-layer chromatography (TLC) profile. Upon evaporation of solvent, 2.8 g. (18% of theory) of oil were collected.

$[\alpha]_D^{25}$ −7.45°(c=0.5, MeOH).

Analysis, Calculated for $C_{15}H_{21}NO_3$ (263.3): C, 68.42; H, 8.04; N, 5.32. Found: C, 68.14; H, 7.86; N, 4.93.

B. 3-Amino-4-phenylbutane-2-one, hydrochloride salt.

The product as prepared in part A (4.4 g., 16.7 mmoles) was dissolved in 50 ml. of glacial acetic acid containing 1.0N HCl (gas) and 5 ml. of anisole. The mixture was stirred at room temperature for 30 minutes after which it was poured into ethyl ether. The resulting precipitate was collected and dried to give 3.1 g. (93%) of the title compound, melting point 131–134° C.

$[\alpha]_D^{25}$ +34.36°(c=0.5, MeOH)

Analysis, Calculated for $C_{10}H_{14}NOCl$ (199.7): C, 60.15; H, 7.07; N, 7.01. Found: C, 60.38; H, 7.02; N, 7.06.

C.

$N^\alpha$-t-Butyloxycarbonyl-L-tyrosyl-D-alanyl-N-(2-oxo-1-benzylpropyl)glycinamide.

$N^\alpha$-Boc-L-Tyr-D-Ala-Gly, dicyclohexylammonium salt (2.96 g.; 0.5 mmoles), was suspended in 20 ml. of DMF, and the mixture was cooled to −15° C. NMM (4 drops) and IBCF (0.66 ml.; 0.5 mmoles) then were added rapidly to the stirring, cooled solution. The solution was stirred at −15° C. during the following preparation:

The product from part B (1 g.; 0.5 mmoles) was dissolved in 5 ml. of DMF. The mixture was cooled to 0° C., and 0.55 ml. (0.5 mmoles) of NMM was added in one portion. The resulting mixture was agitated to ensure complete reaction. The mixture then was added rapidly to the above-prepared solution, and the newly formed mixture was stirred for 4 hours at −15° C. The mixture then was allowed to warm slowly to room temperature over a two-day period. The resulting precipitate was removed by filtration, and the filtrate was concentrated in vacuo to an oil. The oil was dissolved in a mixture of ethyl acetate and 1N aqueous sodium bicarbonate. The organic layer was separated and washed successively with water, 1.5N citric acid, and water. The ethyl acetate layer then was dried over magnesium sulfate and concentrated in vacuo to provide 2.3 g. of the title compound as an oil.

D.

L-Tyrosyl-D-alanyl-N-(2-oxo-1-benzylpropyl)glycinamide, acetate salt

The product from part C (2.3 g.) was dissolved in 15 ml. of trifluoroacetic acid containing 3 ml. of anisole. The mixture was stirred at 0° C. for 30 minutes and then lyophilized to a solid. The solid was dissolved in a buffer composed of 22% acetonitrile and 0.1N ammonium acetate and applied to a 4×70 cm. column containing reverse phase silica gel which had been equilibrated with the same buffer. The eluate was monitored at 280 nm, and the appropriate fractions were combined and lyophilized to provide a white solid. The solid was dissolved in 10 ml. of 0.2M acetic acid and applied to a 2.5×90 cm. Sephadex G-10 column. The column was eluted with 0.2M acetic acid, and the eluate was monitored at 280 nm. The appropriate fractions were combined and lyophilized to provide 773 mg. (37%) of the title compound as a white solid.

$[\alpha]_D^{25}$ +68.97°(c=0.5, 1N HCl)

Analysis, Calculated for $C_{26}H_{34}N_4O_7$ (514.6): C, 60.69; H, 6.66; N, 10.89. Found: C, 60.50; H, 6.80; N, 10.93.

Amino acid analysis; Tyr, 0.99; Ala, 1.01; Gly, 0.99; $NH_3$, 0.21.

EXAMPLE 2

Preparation of
L-Tyrosyl-D-alanyl-N-ethyl-N-(2-oxo-1-benzyl-propyl)glycinamide, acetate salt

A.
3[N-(Ethyl)-t-butyloxycarbamido]-4-phenylbutan-2-one.

$N^\alpha$-t-Butyloxycarbonyl-$N^\alpha$-ethyl-L-phenylalanine (3.4 g.; 0.012 moles) was dissolved in 100 ml. of anhydrous ethyl ether at room temperature and under a nitrogen atmosphere. To the mixture then were added 14.4 ml. (0.023 mole) of 1.6M methyllithium. The mixture was stirred at room temperature for 24 hours after which 10 ml. of water were added over a 10 minute period. The resulting organic layer was separated and washed with 1.5N citric acid followed by water. The ethyl ether solution was dried over magnesium sulfate and evaporated in vacuo to provide 2.6 g. of an oil. The oil was applied in methylene chloride to a 10×2 cm. column containing Grace and Davison grade 62 silica gel. The column was eluted with a step gradient comprising methylene chloride and chloroform [$CH_2Cl_2 \rightarrow CH_2Cl_2/CHCl_3$ (50/50)]. Fractions were combined according to a TLC profile. Upon evaporation of the solvent 1.4 g. (40%) of the title compound were recovered.

NMR $\delta$ (Boc) 1.5, $\delta$ (—$COCH_3$) 2.2, $\delta$ (phenyl) 7.2.

B.
$N^\alpha$-t-Butyloxycarbonyl-D-alanyl-N-ethyl-N-(2-oxo-1-benzylpropyl)glycinamide.

The product from part A (1.3 g.; 4.5 mmoles) was dissolved in 25 ml. of glacial acetic acid containing 1.0N HCl (gas) and 3 ml. of anisole. The mixture was stirred at room temperature for 30 minutes after which it was poured onto a mixture of ethyl ether and petroleum ether. The resulting precipitate was collected and dried to give 1 g. of the hydrochloride salt of 3-ethylamino-4-butan-2-one. This material then was dissolved in 20 ml. of DMF containing 1.19 g. (4.5 mmoles) of $N^\alpha$-t-butyloxycarbonyl-D-alanyl-glycine. The mixture was cooled to 0° C., and 0.9 ml. (4.5 mmoles) of dicyclohexylamine, 0.61 mg. (4.5 mmoles) of HBT, and 0.93 mg. (4.5 mmoles) of DCC were added to the reaction mixture. The mixture was stirred at 0° C. for 6 hours and then at room temperature for 3 days. The mixture then was cooled to 0° C., the precipitate was removed by filtration, and the filtrate was evaporated in vacuo. The resulting residue was dissolved in ethyl acetate, and the ethyl acetate solution was extracted successively with 1N sodium bicarbonate, water, 1.5N citric acid, and water. The organic phase was dried over magnesium sulfate and evaporated in vacuo to obtain 1.3 g. (69%) of the title compound as a solid.

C.
$N^\alpha$-t-Butyloxycarbonyl-L-tyrosyl-D-alanyl-N-ethyl-N-(2-oxo-1-benzylpropyl)glycinamide The product from part B (1.3 g.; 3.1 mmoles) was dissolved in 15 ml. of trifluoroacetic acid containing 3 ml. of anisole. The mixture was stirred for 30 minutes at 0° C. After which the solvent was evaporated in vacuo and without addition of heat. The resulting oil was diluted with ethyl ether. The supernate was decanted, and the remaining oil dried in vacuo.

$N^\alpha$-t-Butyloxycarbonyl-L-tyrosine (871 mg.; 3.1 mmoles) was dissolved in 10 ml. of DMF, and the solution was cooled to −15° C. NMM (0.34 ml.; 3.1 mmoles) and IBCF (0.41 ml.; 3.1 mmoles) were added rapidly to the stirred DMF solution. The solution was stirred at −15° C. while the following was prepared:

The above-prepared trifluoroacetate salt was dissolved in 5 ml. of DMF, and the solution was cooled to −15° C. NMM (0.34 ml.; 3.1 mmoles) was added in one portion, and the solution was agitated to ensure complete reaction. This solution was added to the previously prepared mixed anhydride. The resulting mixture was stirred for 4 hours at −15° C. and then for 24 hours at room temperature. The mixture then was poured into 1N aqueous sodium bicarbonate, and the aqueous solution was extracted with ethyl acetate. The organic phase was separated and extracted successively with water, 1.5N citric acid, and water. The ethyl acetate layer was dried over magnesium sulfate and concentrated in vacuo to obtain 1.2 g. (66%) of the title compound as an oil.

D.
L-Tyrosyl-D-alanyl-N-ethyl-N-(2-oxo-1-benzylpropyl)glycinamide, acetate salt The product from part C (1.2 g.) was dissolved in 20 ml. of trifluoroacetic acid containing 3 ml. of anisole, and the mixture was stirred at 0° C. for 30 minutes. The mixture then was lyophilized to a solid. The resulting solid was dissolved in buffer (20% acetonitrile, 0.1M ammonium acetate at pH 4.0) in an amount sufficient to make a 9.0 ml. solution. The solution was applied to 4×70 cm. column containing reverse phase silica gel which had been equilibrated with the same buffer. The eluate was monitored at 280 nm., and the appropriate fractions were combined and lyophilized to provide a white solid. The solid was dissolved in 10 ml. of 0.2M acetic acid, and the solution was applied to a 2.5×90 cm. Sephadex G-10 column. The column was eluted with 0.2M acetic acid, and the eluate was monitored at 280 nm. The appropriate fractions were combined and lyophilized to provide 509 mg. (46%) of the title compound as a white solid.

$[\alpha]_D^{25}$ +28.3 (c=0.5, MeOH).

Analysis, Calculated for $C_{28}H_{38}N_4O_7$ (542.6): C, 61.98; H, 7.06; N, 10.33. Found: C, 62.00; H, 7.23; N, 10.56.

Amino acid analysis: Tyr, 1.01; Ala, 1.01; Gly, 0.98; $NH_3$, 0.12.

The analgesic activity of the compounds of this invention is demonstrated by the mouse hot plate test. In this test, an upright acrylic cylinder comprising, as its base, a hot plate surface which is maintained at 55° C. is used. A mouse (Harlan ND4) is given, by subcutaneous injection, a predetermined amount of test compound dissolved or suspended in a suitable carrier, and, 15 minutes after administration of the test compound, the mouse is placed on the hot plate surface. The latency in seconds until the mouse jumps from the hot plate surface is measured. An agent which exhibits analgesic activity produces an increase in this latency over that of control mice which receive only the carrier. This must occur in a dose range which produces no motor incoordination or incapacitation. The following Table records ED$_{50}$ results obtained from this test. By the term "ED$_{50}$" is meant that dose which produces analgesia in 50% of the mice tested. Analgesia is defined as a response latency in the presence of test compound that is equal to or greater than the control response latency plus two standard deviations. The percent analgesia data are converted to probits, and the ED$_{50}$ is calculated by regression analysis of the dose-response data. Each dose response curve must have at least four points, and each point is determined using data from a minimum of ten treated mice and ten control mice.

In conjunction with the analgesic activity of the compounds of this invention, they exhibit activity at the enkephalin ($\delta$) receptor. The enkephalin ($\delta$) receptor activity is demonstrated by the recognized mouse vas deferens assay.

In the mouse vas deferens test, single mouse vas deferens from mature mice (Harlan ND4, 30–40 g.) are suspended in 3 ml. of modified Kreb's solution aerated with 95% $O_2$-5% $CO_2$ and maintained at 37° C. The twitch induced by field stimulation (0.15 Hz, 1 msec., 40V) is recorded on a polygraph via an isometric transducer. The test compound is added to the bath in 20 to 30 $\mu$l. aliquots. A dose-response curve is constructed by cumulative addition of appropriate amounts of the compound to the bath. Comparison of relative agonist potency at the $\delta$ receptor is made on the basis of IC$_{50}$ values (concentration causing depression of 50% of the electrically evoked contraction).

The Table following also provides results for compounds of this invention when tested in the mouse vas deferens assay.

TABLE

| H—L-Tyr—D-Ala—Gly—L-(N—R)Phe—Me | | |
|---|---|---|
| Compound R | Mouse Jump ED$_{50}$ mg./kg. | Mouse vas Deferens ($\delta$ receptor) IC$_{50}$, nM |
| H | 3.2 | 0.49 |
| Et | 0.006 | 0.71 |

We claim:
1. A compound of the formula

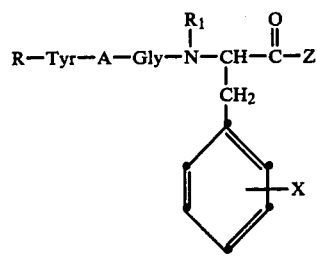

and pharmaceutically acceptable non-toxic acid addition salts thereof, in which

R is hydrogen, methyl, ethyl, cyclopropylmethyl, or allyl;

A is a residue of a D-amino acid selected from the group consisting of Ala, Abu, Nva, Val, Nle, Leu, Ile, Gly(Al), Gly(Cp), Met, Cys(Me), Met(O), Cys(Me)(O), Ser, Ser(Me), Thr, and Hse;

R$_1$ is hydrogen, C$_1$–C$_3$ primary alkyl, cyclopropylmethyl, allyl, ethylthiomethyl, 2-fluoroethyl, or propargyl;

X is fluoro, bromo, iodo, chloro, hydroxy, C$_1$–C$_3$ alkyl, trifluoromethyl, or C$_1$–C$_2$ alkoxy; and Z is methyl or ethyl.

2. Compound of claim 1, in which R is hydrogen.
3. Compound of claim 1, in which Z is methyl.
4. Compound of claim 3, in which X is hydrogen.
5. Compound of claim 4, in which A is Ala, Nva, Val, Nle, Leu, Ile, Met, Met(O), Ser, Ser(Me), Thr, or Hse.
6. Compound of claim 5, in which A is Ala, Met, Met(O), Ser(Me), Nva, or Nle.
7. Compound of claim 6, in which A is Ala.
8. Compound of claim 7, in which R$_1$ is C$_1$–C$_3$ primary alkyl, cyclopropylmethyl, allyl, or propargyl.
9. Compound of claim 8, in which R$_1$ is ethyl, cyclopropylmethyl, allyl, or propargyl.
10. Compound of claim 9, in which R$_1$ is ethyl.
11. Compound of claim 10, in which R is hydrogen.
12. Compound of claim 10, in which R is methyl.
13. Compound of claim 9, in which R$_1$ is hydrogen.
14. Compound of claim 13, in which R is hydrogen.
15. Compound of claim 13, in which R is methyl.

* * * * *